United States Patent
Chen

(10) Patent No.: US 9,107,982 B2
(45) Date of Patent: *Aug. 18, 2015

(54) CULTURED TISSUE TRANSPLANT DEVICE

(76) Inventor: Paul Hong-Dze Chen, Rancho Santa Fe, CA (US)

( * ) Notice: Subject to any disclaimer, the term of this patent is extended or adjusted under 35 U.S.C. 154(b) by 662 days.

This patent is subject to a terminal disclaimer.

(21) Appl. No.: 13/436,255

(22) Filed: Mar. 30, 2012

(65) Prior Publication Data

US 2012/0191184 A1 Jul. 26, 2012

Related U.S. Application Data

(63) Continuation-in-part of application No. 11/270,942, filed on Nov. 9, 2005, now Pat. No. 8,158,141.

(51) Int. Cl.
| | |
|---|---|
| A61F 2/00 | (2006.01) |
| A61L 27/38 | (2006.01) |
| A61L 15/28 | (2006.01) |
| A61L 15/32 | (2006.01) |
| A61L 15/40 | (2006.01) |
| A61L 15/58 | (2006.01) |
| A61L 27/36 | (2006.01) |
| A61L 31/00 | (2006.01) |

(52) U.S. Cl.
CPC ............. *A61L 27/3804* (2013.01); *A61L 15/28* (2013.01); *A61L 15/32* (2013.01); *A61L 15/40* (2013.01); *A61L 15/58* (2013.01); *A61L 27/3604* (2013.01); *A61L 27/3869* (2013.01); *A61L 31/005* (2013.01); *A61L 2300/64* (2013.01); *A61L 2430/16* (2013.01)

(58) Field of Classification Search
None
See application file for complete search history.

(56) References Cited

U.S. PATENT DOCUMENTS

| | | | |
|---|---|---|---|
| 4,983,181 A | 1/1991 | Civerchia | |
| 4,994,081 A | 2/1991 | Civerchia et al. | |
| 5,000,963 A | 3/1991 | Hefton | |
| 5,112,350 A | 5/1992 | Civerchia et al. | |
| 5,489,304 A | 2/1996 | Orgill et al. | |
| 5,522,888 A | 6/1996 | Civerchia | |
| 5,643,187 A | 7/1997 | Næstoft et al. | |
| 5,654,135 A | 8/1997 | Tinois et al. | |
| 5,693,332 A | 12/1997 | Hansbrough | |
| 5,712,137 A | 1/1998 | Barlow et al. | |
| 5,716,411 A | 2/1998 | Orgill et al. | |
| 5,716,633 A | 2/1998 | Civerchia | |
| 6,039,972 A | 3/2000 | Barlow et al. | |
| 6,093,868 A | 7/2000 | Sawano et al. | |
| 6,187,053 B1 | 2/2001 | Minuth | |
| 6,274,787 B1 | 8/2001 | Downing | |
| 6,296,867 B1 | 10/2001 | Peyman | |
| 6,333,029 B1 | 12/2001 | Vyakarnam et al. | |
| 6,534,084 B1 | 3/2003 | Vyakarnam et al. | |
| 6,541,028 B1 | 4/2003 | Kuri-Harcuch et al. | |
| 6,793,677 B2 | 9/2004 | Ferree | |
| 6,821,107 B1 | 11/2004 | Hara et al. | |
| 6,880,558 B2 | 4/2005 | Perez | |
| 2003/0018347 A1 | 1/2003 | Pallikaris et al. | |

OTHER PUBLICATIONS

He YG, McCulley JP "Growing human corneal epithelium on collagen shield & subsequent transfer to denuded cornea in vitro" [abstract], CurrEyeRes. Sep. 1991;10(9):851-63, Texas(US).

McCulley JP, et al., "in vitro transfer of rabbit corneal epithelium from carriers to denuded corneas or cryolathed lenticules"[abstract], Cornea. Nov. 1991;10(6):466-77, Texas.

"Fibrin Sealant in Corneal Stem Cell Transplantation" [abstract], Ophthalmology Review, Jun. 28, 2005, Cornea. 24(5): 593-598, Jul. 2005.

M Iwata, et al. "Intercellular adhesion molecule-1 expression on human corneal epithelial outgrowth from limbal explant in culture" British Jour.of Ophthalmology 2003;87:203-7.

Yu-Guang He et al. Growing Human Corneal Epithelium on Collagen Shield and Subsequent Transfer to Denuded Cornea in Vitro, *Current Eye Research*, vol. 10, No. 9, Oxford University Press (1991), 13 pages.

*Primary Examiner* — Kade Ariani
(74) *Attorney, Agent, or Firm* — Knobbe, Martens, Olson & Bear, LLP

(57) ABSTRACT

A device for transplanting a graft such as a layer or layers of cultivated, autologous, allogenic or xenogenic cells to cover an accidental or surgical wound. The graft is cultivated and carried on a bed of collagen or other dissolvable or releasable material mounted on a protective substrate molded to conform to the profile of the wounded area and provided with a lateral attachment zone. The device facilitates the graft cultured in vitro to the recipient surface.

36 Claims, 6 Drawing Sheets ically ablated; after which, the epithelial layer is either discarded or flipped back over the laser-corrected area.

CULTURED TISSUE TRANSPLANT DEVICE

RELATED PRIORITY APPLICATIONS

This application is a continuation-in-part of U.S. Ser. No. 11/270,942 filed on Nov. 9, 2005, which is hereby incorporated by reference in its entirety.

FIELD OF THE INVENTION

The invention relates to the culturing of grafts and other healing tissues and to their transfer and anchoring, upon a wounded area.

BACKGROUND

A corrective eye surgery such as laser photo-refractive keratectomy requires the peeling away of the corneal epithelial layer before the underlying stroma tissue is selectively ablated; after which, the epithelial layer is either discarded or flipped back over the laser-corrected area.

In the course of the procedure, the epithelial layer is subject to be torn or crinkled to the point where the ablated area is not fully covered by epithelial cells and subject to contamination and uneven healing or the epithelial layer has been too mechanically traumatized to be viable.

Epithelial cells, dermis or epidermis are now routinely cultured and placed over burns and other wounded areas as disclosed in U.S. Pat. No. 6,541,028 which is incorporated in this Specification by reference. The handling of the graft and its correct positioning over the wound requires great dexterity on the part of the surgeon in order to avoid damaging of the graft and improper coverage of the wound. Furthermore, movement of the graft on the wound after application often causes graft failure due to poor adhesion or mechanical movement and trauma.

The re-connection of severed nerves, tendons, blood vessels, and other filiform tissues is commonly enhanced by the use of scaffolding material such as a mesh sleeve into which the ends of the severed tissue can grow and reconnect. When dealing with very small filiform tissues such as nerves, the construction and handling of the scaffolding structure becomes extremely difficult due to the smallness of the severed tissue and the available work zone.

The instant embodiments provide structural implements that can facilitate the culturing, transfer and installation of grafts without compromising their integrity.

SUMMARY OF THE INVENTION

The instant embodiments provide a carrier upon which a graft or healing tissue such as a monolayer or polylayer of cells can be cultured then transported and intimately and accurately positioned upon an accidental or surgical wound. The carrier is particularly useful in the culturing and grafting of a layer of cells to a mammalian subject whose cornea has been ablated in the course of a photo-refractive keratectomy operation after removal of the epithelial cover.

In one embodiment, the carrier is a molded substrate in the shape of a dome of which a posterior, concave section is shaped and dimensioned to accurately match the profile of a human cornea. A releasable layer of dissolvable collagen interposed between the molded substrate and the epithelial cells facilitates the release of the cell upon the accidentally wounded or surgically ablated cornea. A lateral portion of the substrate projects peripherally and is coated with an adhesive or is sutured to the corneal limbus or sclera. In some embodiments a central portion of the substrate is coated with an adhesive or is sutured to the corneal limbus or sclera.

The substrate can be formed in the shape of an ophthalmic conformer bearing patches of ophthalmologically safe adhesive. The shape of an ophthalmic conformer helps minimize graft movement on the eye and facilitates cell adhesion and transfer. Alternatively, the substrate may be sutured to minimize graft movement on the eye and enhance cell adhesion.

In another one of the instant embodiments, channels are cut into a posterior face of a slab of biocompatible material, and dimensioned and oriented to intimately nest a damaged nerve or other filiform tissue. The second slab of biocompatible material is shaped in a mirror image of the first one, and joined to it to form a pair of clamping shells that completely surround the damaged tissue. Fenestrations drilled between the channel and the anterior face of each slab provide tunnels through which branches of the nerve can grow.

Alternatively, in yet other embodiments cultured nerve cells can be grown in the channels and the ends of the damaged nerves can be attached to the edges of the device. The anterior fenestrated face of each slab can be placed over the target effector tissue such as a muscle group.

Other embodiments provide a live tissue transplant device which comprises: a substrate having an active posterior face and an opposite anterior face; said posterior face having a central active zone and a lateral zone; said active zone comprising: a releasable support layer, and a layer of cells cultured upon said device and spread over said support layers; and said posterior face comprising means for securing said substrate around a wound.

Alternatively, in yet other embodiments a live tissue transplant device comprises: a substrate having a central zone and a lateral zone peripheral to the central zone, where in the central zone comprises a concave posterior face and a convex anterior face; said concave posterior face comprising: a releasable support layer and living, transplantable cells embedded upon the releasable layer; and means for attaching the substrate around a wound. An attacher is configured for securing the substrate around a wound. The attacher is optionally a patch of adhesive. In another embodiment, the attacher is at least one suture. In some embodiments, the device further comprises of an optional layer of viscoelastic placed upon the transplantable cells or releasable layer.

In some embodiments said substrate comprises a sheet of material. In some embodiments said attachment zone comprises a peripheral margin of said sheet. In some embodiments said means for attaching comprise at least one patch of adhesive material applied to said peripheral margin. In some embodiments said means for attaching the substrate around the wound comprises embedded sutures within the substrate. In some embodiments the sutures may be embedded in the central zone. In some embodiments, the sutures are embedded in the lateral zone. In some embodiments said substrate comprises a molded body shaped and dimensioned to conform to the profile of said tissue. In some embodiments said body defines a dome having a concave posterior face dimensioned to intimately mate with a section of a cornea. In some embodiments said body has a channel cut in said posterior face, said channel being dimensioned to receive a filiform tissue. In some embodiments said substrate comprises a slab of biocompatible material.

In some embodiments the device has fenestrations between said channel and said anterior face. In some embodiments a second device is provided which is shaped and dimensioned as a mirror image thereof, wherein said devices are joined about their posterior faces to form a tunnel around a filiform tissue. In some embodiments said channel is shaped and dimensioned to nest a nerve section. Yet other embodiments further comprise means for dissolving said support layer. In one embodiment, the means for dissolving said support layer comprises a dissolving agent. Suitable dissolving agents include collagenase, gelatinase, hyaluronidase, trypsin, papain, and other proteases. In some embodiments the support layer is selected from the group consisting of collagen, amnionic membrane, cellulose, gelatin, and agarose. In some embodiments said adhesive material is fibrin, cyanoacrylate, or combinations thereof.

In some embodiments the device further comprises at least one partition projecting from said posterior face and dividing said active zone into separate areas. In some embodiments the device further comprises a viscoelastic layer placed upon said transplantable cells or releasable layer. In some embodiments said substrate is formed in the shape of an ophthalmic conformer. In some embodiments said substrate is formed in the shape of a contact lens. In some embodiments said substrate comprises adhesive patches astride said support layer. Some embodiments further comprise a peripheral skirt surrounding said support layer.

Still further embodiments provide a method, for culturing, transplanting and securing a graft over a surgically or accidentally wounded area, which comprises: procuring a first substrate having an outer face and an inner face, said inner face being shaped and dimensioned to conform to the shape of said area; coating a portion of said inner face with a sheet of releasable biocompatible material; culturing at least one layer of live tissue cells upon or embedded within the said sheet; applying said substrate sheet and layer to said area; and securing said substrate to said area.

In some embodiments, the releasable layer is selected from the group consisting of collagen, amnionic membrane, cellulose, gelatin and agarose. In some embodiments said layer comprises epithelial cells. In some embodiments live tissue cells are embedded within the releasable layer as disclosed in Enami et al. U.S. Pat. No. 5,264,359 issued Nov. 23, 1993, herein incorporated by reference, and said area consists of a cornea of a mammalian subject. In some embodiments said substrate is molded in the shape of a contact lens. In some embodiments said substrate is molded in the shape of an ophthalmic conformer. In some embodiments said substrate is molded in the shape of an adhesive skin bandage. In some embodiments said epithelial cells are autologous, allogenic or xenogenic to said subject. In some embodiments the method further comprises procuring a pair of said coated and layered substrates, one being a mirror image of the other, clamping said substrates together over a filiform tissue. In some embodiments said area consists of a cornea of mammalian subject and said layer comprises pumping cells selected from the group consisting of endothelial cells, kidney cells, gastric cells, intestinal cells and colon cells. In some embodiments said pumping cells are autologous, allogenic or xenogenic to said subject. In some embodiments said layer comprises stem cells. In some embodiments said stem cells are autologous, allogenic or xenogenic. In some embodiments said layer comprises cultured cartilage, bone, synovial, periostial, or marrow cells. In some embodiments said live tissue cells are autologous, allogenic or xenogenic. In some embodiments said layer comprises cultured neuron or glial cells, and said area comprises neural tissue of a mammalian subject. In some embodiments said live tissue cells are autologous, allogenic or xenogenic. In some embodiments said layer comprises epithelium, fibroblasts, or endothelium, and said area comprises skin of a mammalian subject. In some embodiments said live tissue cells are autologous, allogenic or xenogenic. In some embodiments said layer comprises smooth muscle cells, striated muscle cells, or cardiac muscle cells, and said area comprises muscle of a mammalian subject. In some embodiments said live tissue cells are autologous, allogenic or xenogenic. In some embodiments said layer comprises cardiac muscle cells, and said area comprises cardiac muscle of a mammalian subject. In some embodiments said cardiac muscle cells are autologous, allogenic or xenogenic.

DETAILED DESCRIPTION OF THE PREFERRED EMBODIMENT

Figure 1A:
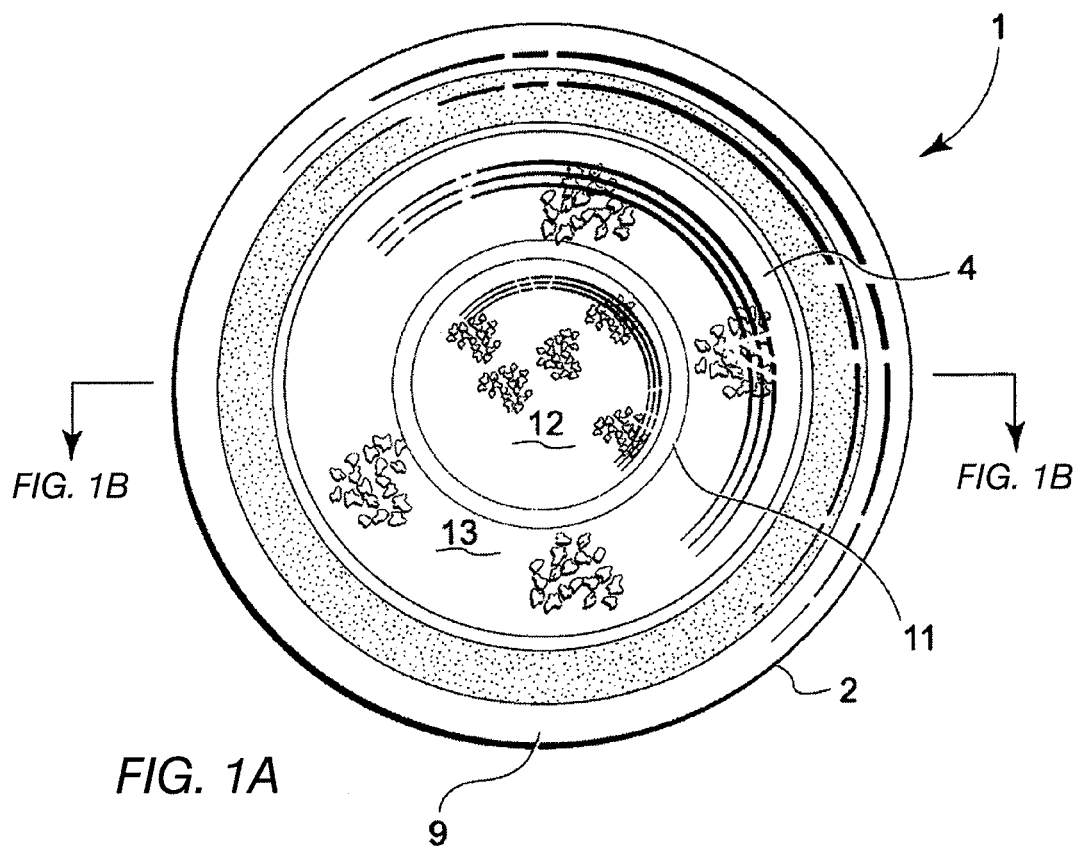
FIG. 1A is a diagrammatical plan view of the posterior face of a first embodiment of the invention.
Figure 1B:
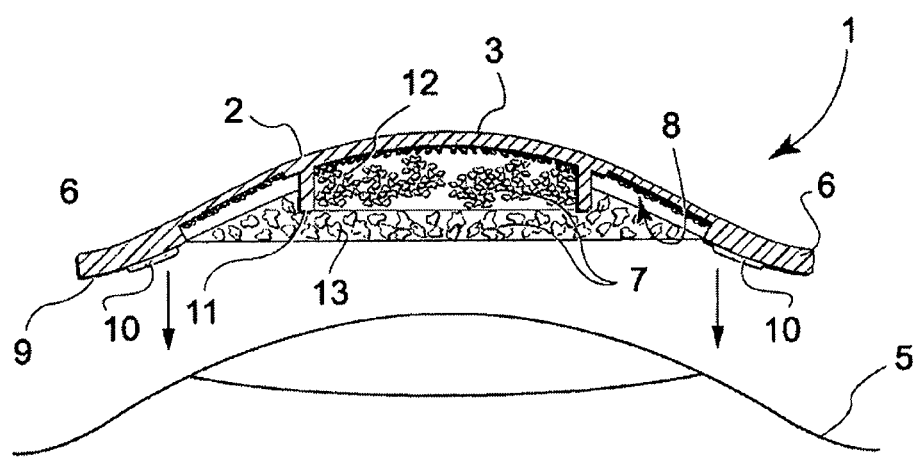
FIG. 1B is a cross-sectional view of FIG. 1A.
Figure 2A:
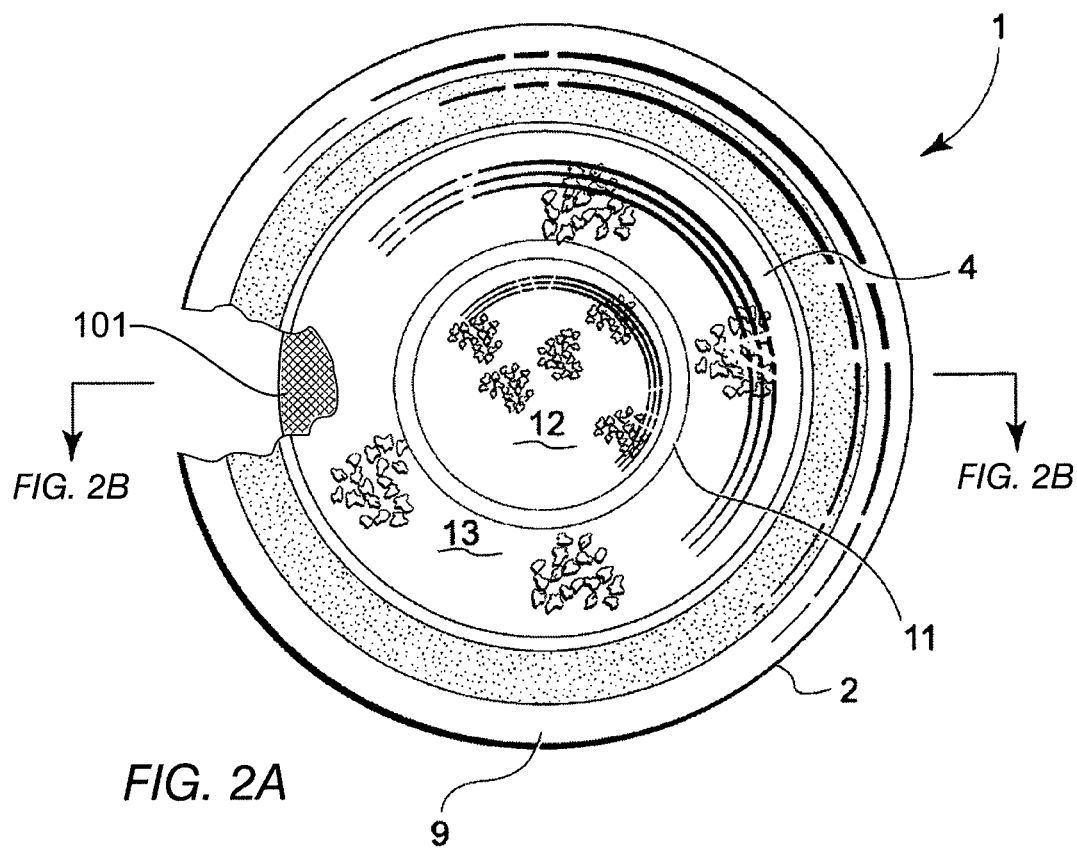
FIG. 2A is a diagrammatical plan view of the posterior face of a first embodiment of the invention with illustration of optional viscoelastic layer.
Figure 2B:
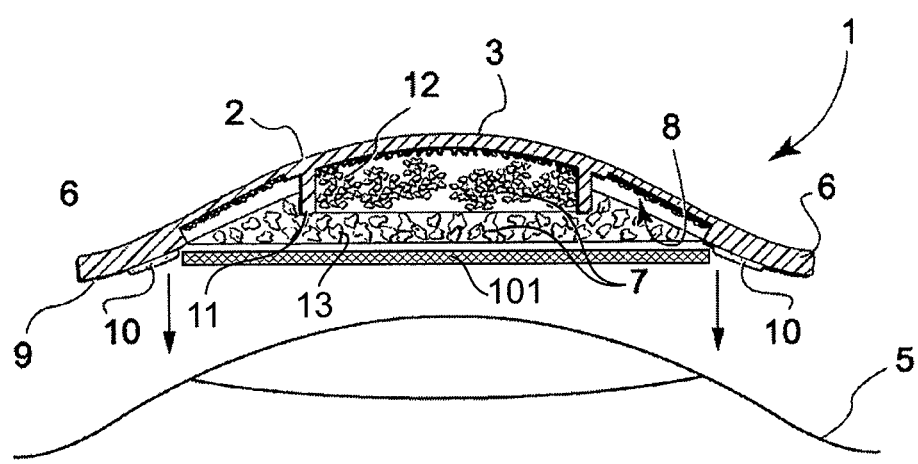
FIG. 2B is a cross-sectional view of FIG. 2A.

In the following detailed description, only certain exemplary embodiments of the present disclosure have been shown and described, simply by way of illustration. As those skilled in the art would realize, the described embodiments may be modified in various different ways, all without departing from the spirit or scope of the present disclosure. Accordingly, the drawings and description are to be regarded as illustrative in nature and not restrictive. In addition, when an element is referred to as being "on" another element, it can be directly on the another element or be indirectly on the another element with one or more intervening elements interposed therebetween. Also, when an element is referred to as being "connected to" another element, it can be directly connected to the another element or be indirectly connected to the another element with one or more intervening elements interposed therebetween. Hereinafter, like reference numerals refer to like elements.

Hereinafter, embodiments of the disclosure will be described with reference to the attached drawings. Without particular definition or mention provided, terms that indicate directions used to describe the disclosure are based on the state shown in the drawings. Further, the same reference numerals indicate the same members in the embodiments. On the other hand, a thickness or a size of each component displayed on the drawings may be exaggerated for the convenience of the description, which does not mean that it should be estimated by the ratio between its size and the component.

Features of the present disclosure will become more fully apparent from the following description and appended claims, taken in conjunction with the accompanying drawings. It will be understood these drawings depict only certain embodiments in accordance with the disclosure and, therefore, are not to be considered limiting of its scope; the disclosure will be described with additional specificity and detail through use of the accompanying drawings. An apparatus, system or method according to some of the described embodiments can have several aspects, no single one of which necessarily is solely responsible for the desirable attributes of the apparatus, system or method. After considering this discussion, and particularly after reading the section entitled "Detailed Description of Preferred Embodiments" one will understand how illustrated features serve to explain certain principles of the present disclosure.

Referring now to the drawing, there is shown in FIGS. 1A, 1B, 2A, and 2B live tissue culturing, transferring and installing device 1 according to the invention. The device comprises a molded, transparent substrate 2 shaped in the form of a dome 3 akin to a contact lens whose inner or posterior, concave face 4 is dimensioned to intimately mate with a surface section 5 of a mammalian cornea and sclera. Extending peripherally from the outer edge of the dome section 3 is lateral skirt portion forming a peripheral margin 6 which projects slightly posteriorly to contact the cornea or the sclera when the device is in place.

The substrate is preferably made of silicone, hydrogel, acrylate-hydrogel, silicone-acrylate, fluro-silicone acrylate or other ophthalmologically acceptable material known to those of ordinary skill in the art of contact lens manufacture.

In the process of a photo-refractive keratectomy operation, a central section of the corneal epithelial layer is completely removed before the corrective ablation of the underlying stromal tissue. One or more layers of cultured cells 7 are seeded upon a bed 8 of collagen coating the posterior or inner face 4 of the substrate. Alternatively, one or more layers of cultured cells 7 are embedded within the collagen layer 8. The bed or layer of collagen 8 is designed to facilitate the release of the epithelial cell upon the cornea 5. Other dissolvable or otherwise releasable biocompatible material may be used such as cellulose, gelatin, agarose, amnionic membrane, or other medium known to those with ordinary skill in the art, including such techniques in which the apical adhesion molecules of the epithelial cells in contact with the substrate can be released and the basal adhesion molecules in contact with the corneal stroma can be selectively released with the use of an antibiotic sensitive promoter. The posterior face 9 of the skirt 6 is preferably slightly textured to improve adhesion, and coated with a biocompatible glue 10 such as fibrin, cyanoacrylate, and other such ophthalmologically acceptable adhesive.

Optionally, one or more partitions 11 may project posteriorly from the substrate to separate diverse groups of culture cells. For example, the center section 12 may carry transparent epithelial cells to replace the removed section, while the peripheral annular section 13 may carry some healing culture such as stem cells, kidney cells, gastric cells, intestinal cells, colon cells, or corneal endothelial cells which pump fluid out of the cornea to maintain corneal clarity and minimize corneal edema.

Optionally, a layer of viscoelastic material 101 may be placed upon the layer of cultured cells or releasable layer, such as collagen 8 comprising embedded cells to protect the cells from mechanical trauma during the transplantation process. In one embodiment the viscoelastic material may be made of hyaluronic acid, chondroitin sulfate or any ophthalmologically acceptable viscoelastic composition known to those of ordinary skill in the art.

The transparent substrate, collagen and cultured cells do not obstruct vision and provide an effective shield that prevents the cornea from touching debris or infective material.

Figure 3:
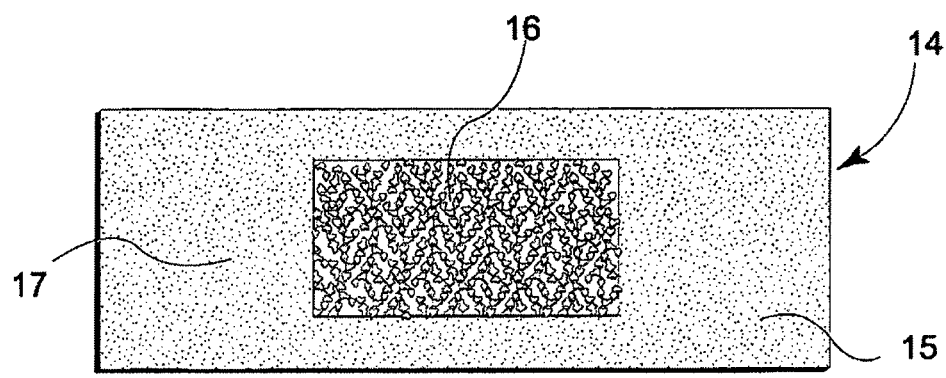
FIG. 3 is a diagrammatical plan view of the posterior face of a second embodiment of the invention.
Figure 4A:
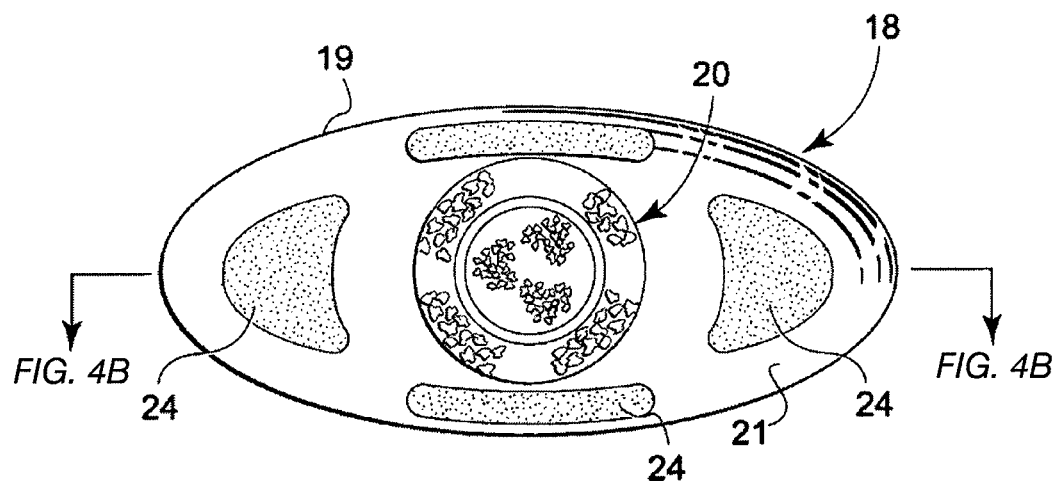
FIG. 4A is a diagrammatical plan view of the posterior face of a third embodiment of the invention.
Figure 4B:
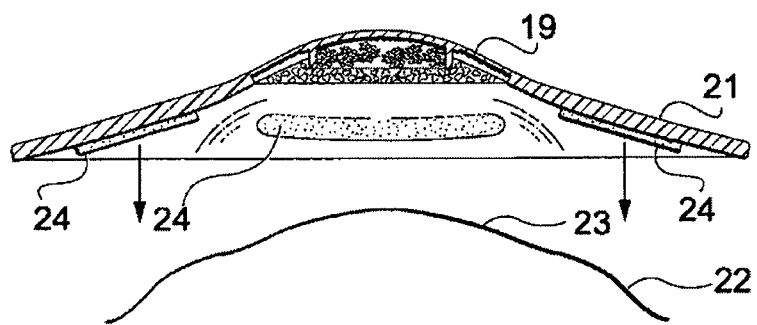
FIG. 4B is a cross sectional view of FIG. 4A.
Figure 5A:
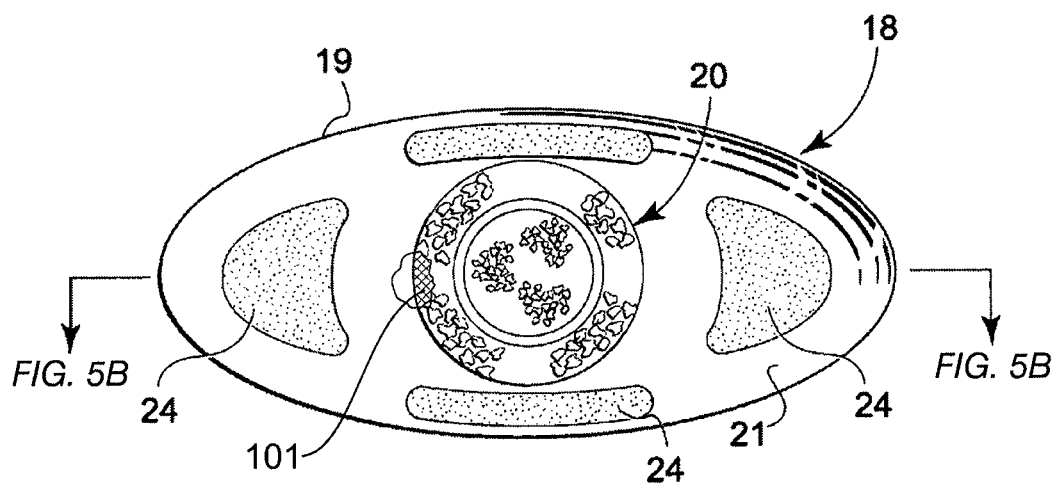
FIG. 5A is a diagrammatical plan view of the posterior face of a third embodiment of the invention with illustration of optional viscoelastic layer.
Figure 5B:
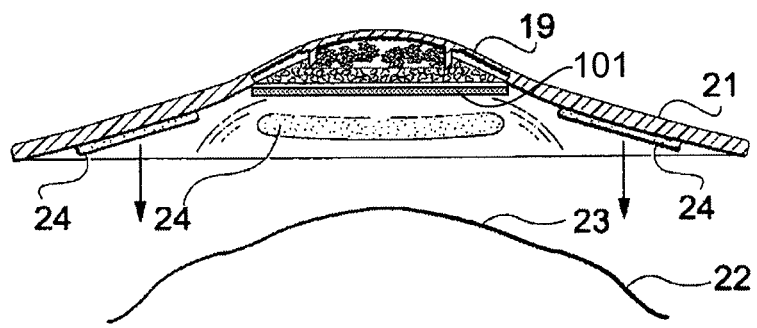
FIG. 5B is a cross sectional view of FIG. 5A.

FIG. 3 illustrates a first alternate embodiment in which the substrate 15 is a pliable or rigid sheet of material carrying in its center a patch 16 of cultured cells over a bed of releasable material as previously described in connection with the first embodiment of the invention. Alternatively, in some embodiments the cultured cells may be embedded within the releasable material 8. The substrate may be made in the shape of a common adhesive skin bandage. Patches 17 of biocompatible glue facilitate the adhesion of the substrate to skin, muscles, bones or other tissues of which a damaged area is covered by the cultured layer 16. Alternatively, the slab may be made of a biocompatible porous foam material which may be placed on the surface of the body, or implanted within the body, in which it may be permanent or dissolvable.

FIGS. 4A, 4B, 5A and 5B illustrate a second alternate embodiment 18 in which the substrate 19 is formed in the shape of an ophthalmic conformer. The central portion of the device 20 is essentially similar to the one described in connection with the first embodiment. However, the peripheral skirt of the first embodiment is replaced here by a lateral projection 21 that extends peripherally to cover the sclera and limbus 22 of the cornea 23. Patches 24 of biocompatible glue are used to secure the device over the cornea. Alternatively, in some embodiments sutures are embedded within the removable substrate to secure the device over the cornea. The shape of the ophthalmic conformer matches the shape of the eye socket and minimizes movements of the device, thus maximizing adhesion and transfer of the cells.

Figure 6:
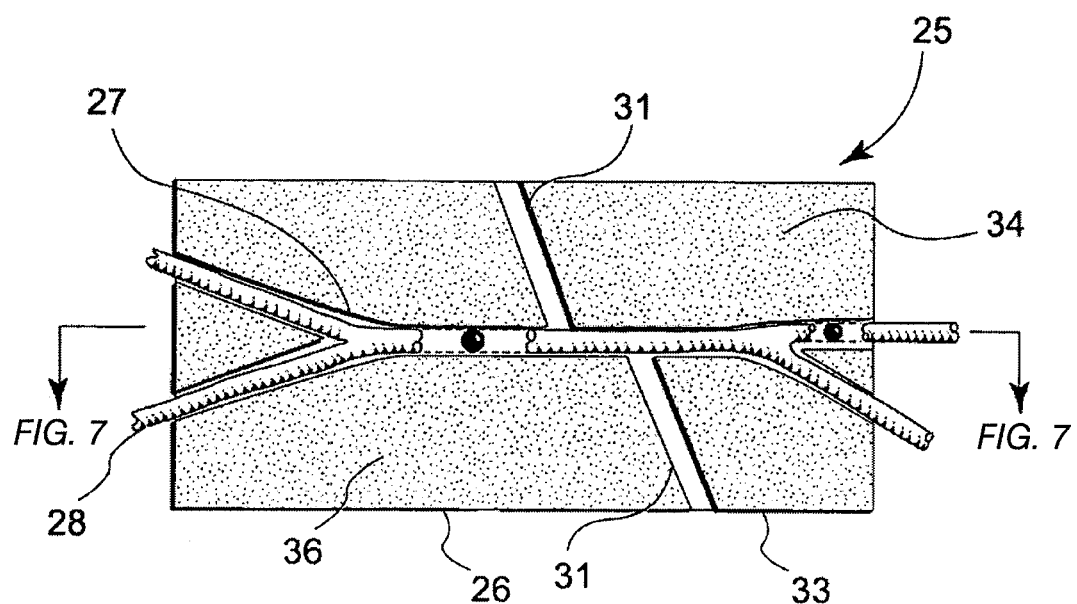
FIG. 6 is a diagrammatical plan view of the posterior face of a fourth embodiment of the invention.
Figure 7:
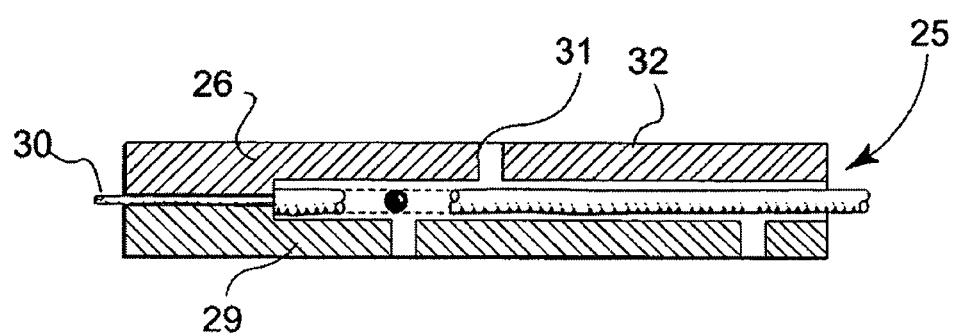
FIG. 7 is a diagrammatical cross-sectional view of a nerve healing device using mirror images of the fourth embodiment of FIG. 6.

FIGS. 6 and 7 illustrate a third alternate embodiment particularly adapted to promote the healing of sections of filiform tissues such as a nerve, tendon, or blood vessel. The first slab 26 of polymer or other biocompatible material has a gutter or channel 27 carved into its posterior face 34. The channel 27 is shaped and dimensioned to conform to the shape of a nerve 28 or other filiform tissue. The channel is pre-seeded with cultured neurons and/or cultured glial cells. A second slab 29 of the same material as the first is shaped and dimensioned as a mirror image of the first slab 26 whereby the two slabs can be joined together about their posterior faces to form two clamping shells sandwiching the nerve section 28 therebetween. A layer of glue 30 is used to hold the two slabs together. Fenestration 31 between the channel 27 and the anterior face 32 and lateral faces 33 of the slabs form tunnels through which neurological branches can grow. Alternately, the slab may be made of a porous foam material which can serve as a scaffolding for the growth of filiform tissues.

Alternatively, cultured neuron and/or cultured glial cells can be grown in the channels 27, and the ends of the damaged nerves 28 can be attached to the edges of the device 25 with sutures or biocompatible glue. The anterior fenestrations 31 can be placed over a target effector tissue such as a muscle group.

In each of the above-described embodiments, the cultured layer may comprise cultured stem cells to promote healing and regeneration.

While the present disclosure has been described in connection with certain exemplary embodiments, it will be appreciated by those skilled in the art that various modifications and changes may be made without departing from the scope of the present disclosure. The drawings and the detailed description of certain inventive embodiments given so far are only illustrative, and they are only used to describe certain inventive embodiments, but are should not used be considered to limit the meaning or restrict the range of the present disclosure described in the claims. Indeed, it will also be appreciated by those of skill in the art that parts included in one embodiment are interchangeable with other embodiments; one or more parts from a depicted embodiment can be included with other depicted embodiments in any combination. For example, any of the various components described herein and/or depicted in the Figures may be combined, interchanged or excluded from other embodiments. With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. Therefore, it will be appreciated to those skilled in the art that various modifications may be made and other equivalent embodiments are available. Accordingly, the actual scope of the present disclosure must be determined by the spirit and scope of the appended claims, and equivalents thereof.

What is claimed is:

1. A living cell transplant device for treatment of a surgical or accidental corneal wound, wherein the device comprises:
    a. a removable substrate formed in the shape of an ophthalmic conformer having a central zone and a lateral zone peripheral to the central zone, wherein the central zone comprises a concave posterior face and a convex anterior face, and wherein the substrate further comprises an ophthalmologically acceptable material;
    b. a releasable layer, coating the concave posterior face;
    c. a plurality of living, transplantable cells upon the releasable layer, wherein the releasable layer is designed to facilitate release of the living, transplantable cells upon the corneal wound to effect transplantation thereof; and
    d. means for attaching the substrate formed in the shape of an ophthalmic conformer around the wound.

2. The device of claim 1, wherein the means for attaching the substrate in the form of an ophthalmic conformer comprises at least one patch of adhesive material applied to the posterior face.

3. The device of claim 1, which further comprises a means for dissolving the releasable layer.

4. The device of claim 1, wherein the releasable layer is selected from the group consisting of collagen, amniotic membrane, cellulose, gelatin, and agarose.

5. The device of claim 2, wherein the adhesive material is selected from the group consisting of fibrin and cyanoacrylate.

6. The device of claim 1, which further comprises at least one partition projecting from the concave posterior face and dividing the central zone into separate areas.

7. The device of claim 1, wherein the means for attaching the removable substrate formed in the shape of an ophthalmic conformer is at least one embedded suture in the central zone.

8. The device of claim 1, wherein the means for attaching the removable substrate formed in the shape of an ophthalmic conformer is at least one embedded suture in the lateral zone.

9. The device of claim 1, which further comprises a protective viscoelastic layer.

10. The device of claim 1, wherein said dissolving means is selected from the group consisting of collagenase, gelatinase, hyaluronidase, trypsin, and papain.

11. A living cell transplant device for treatment of a surgical or accidental corneal wound, wherein the device comprises:
    a. a removable substrate formed in the shape of an ophthalmic conformer having a central zone and a lateral zone peripheral to the central zone, wherein the central zone comprises a concave posterior face and a convex anterior face, and wherein the substrate further comprises an ophthalmologically acceptable material;
    b. a releasable layer, coating the concave posterior face;
    c. a plurality of living, transplantable cells embedded within the releasable layer, wherein the releasable layer is designed to facilitate release of the living, transplantable cells upon the corneal wound to effect transplantation thereof; and
    d. an attacher, wherein said attacher attaches the substrate formed in the shape of an ophthalmic conformer around the wound.

12. The device of claim 11, wherein the attacher comprises at least one patch of adhesive material applied to the posterior face.

13. The device of claim 11, further comprising a dissolving agent for dissolving the releasable layer.

14. The device of claim 11, wherein the releasable layer is selected from the group consisting of collagen, amniotic membrane, cellulose, gelatin, and agarose.

15. The device of claim 12, wherein the adhesive material is selected from the group consisting of fibrin and cyanoacrylate.

16. The device of claim 11, which further comprises at least one partition projecting from the concave posterior face and dividing the central zone into separate areas.

17. The device of claim 11, wherein the attacher comprises embedded sutures in the central or lateral zone.

18. The device of claim 11, which further comprises a protective viscoelastic layer placed upon the releasable layer.

19. A living cell transplant device for treatment of a surgical or accidental corneal wound, wherein the device comprises:
    a. a removable substrate formed in the shape of a contact lens having a central zone and a lateral zone peripheral to the central zone, wherein the central zone comprises a concave posterior face and a convex anterior face, and wherein the substrate further comprises an ophthalmologically acceptable contact lens material;
    b. a releasable layer, coating the concave posterior face;
    c. a plurality of living, transplantable cells upon the releasable layer, wherein the releasable layer is designed to facilitate release of the living, transplantable cells upon the corneal wound to effect transplantation thereof; and
    d. an attacher for attaching the substrate formed in the shape of a contact lens around the wound.

20. The device of claim 19, wherein the attacher comprises at least one patch of adhesive material applied to the posterior face.

21. The device of claim 19, which further comprises a dissolving agent for dissolving the releasable layer.

22. The device of claim 19, wherein the releasable layer is selected from the group consisting of collagen, amniotic membrane, cellulose, gelatin, and agarose.

23. The device of claim 20, wherein the adhesive material is selected from the group consisting of fibrin and cyanoacrylate.

24. The device of claim 19, which further comprises at least one partition projecting from the concave posterior face and dividing the central zone into separate areas.

25. The device of claim 19, wherein the attacher comprises embedded sutures in the central zone.

26. The device of claim 19, wherein the attacher comprises embedded sutures in the lateral zone.

27. The device of claim 19, which further comprises a protective viscoelastic layer placed upon the releasable layer.

28. A living cell transplant device for treatment of a surgical or accidental corneal wound, wherein the device comprises:
   a. a removable substrate formed in the shape of a contact lens having a central zone and a lateral zone peripheral to the central zone, wherein the central zone comprises a concave posterior face and a convex anterior face, and wherein the substrate further comprises an ophthalmologically acceptable contact lens material;
   b. a releasable layer, coating the concave posterior face;
   c. a plurality of living, transplantable cells embedded within the releasable layer, wherein the releasable layer is designed to facilitate release of the living, transplantable cells upon the corneal wound to effect transplantation thereof; and
   d. an attacher for attaching the substrate formed in the shape of a contact lens around the wound.

29. The device of claim 28, wherein the attacher comprises at least one patch of adhesive material applied to the posterior face.

30. The device of claim 28, which further comprises a dissolving agent for dissolving the releasable layer.

31. The device of claim 28, wherein the releasable layer is selected from the group consisting of collagen, amniotic membrane, cellulose, gelatin, and agarose.

32. The device of claim 29, wherein the adhesive material is selected from the group consisting of fibrin and cyanoacrylate.

33. The device of claim 28, which further comprises at least one partition projecting from the concave posterior face and dividing the central zone into separate areas.

34. The device of claim 28, wherein the attacher comprises embedded sutures in the central zone.

35. The device of claim 28, wherein the attacher comprises embedded sutures in the lateral zone.

36. The device of claim 28, which further comprises a protective viscoelastic layer placed upon the releasable layer.

* * * * *